(12) United States Patent
Chen et al.

(10) Patent No.: US 6,830,924 B1
(45) Date of Patent: Dec. 14, 2004

(54) ISOLATED NUCLEIC ACID MOLECULE ENCODING CANCER ASSOCIATED ANTIGENS, THE ANTIGENS PER SE, AND USES THEREOF

(75) Inventors: Yao-Tseng Chen, New York, NY (US); Ali Gure, New York, NY (US); Solam Tsang, New York, NY (US); Elisabeth Stockert, New York, NY (US); Elke Jager, Frankfurt AM Main (DE); Alexander Knuth, Frankfurt AM Main (DE); Lloyd J. Old, New York, NY (US)

(73) Assignees: Ludwig Institute for Cancer Research, New York, NY (US); Memorial Sloan-Kettering Cancer Center, New York, NY (US); Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/270,437

(22) Filed: Mar. 16, 1999

Related U.S. Application Data

(63) Continuation-in-part of application No. 09/061,709, filed on Apr. 17, 1998, now Pat. No. 6,297,364.

(51) Int. Cl.$^7$ ................. C12N 15/63; C12N 5/16; C12N 1/20; C12N 1/21; C07H 21/04
(52) U.S. Cl. ................. 435/320.1; 435/252.3; 435/254.11; 435/325; 536/23.5; 536/24.33
(58) Field of Search ............ 435/320.1, 252.3, 435/254.11, 325; 536/23.5, 24.33; 436/64; 514/44

(56) References Cited

U.S. PATENT DOCUMENTS 6,255,055 B1 * 7/2001 Ross .................. 435/7.1

OTHER PUBLICATIONS

Falk et al, Nature, 1991, vol. 351, pp. 290–296.*
Rotzschke et al, Nature, 1990, vol. 348, pp. 252–254.*
Bjorkman et al, Nature, 1987, vol. 329, pp. 512–518.*
Cell, 1993, vol. 74, pp. 929–937.*
Journal of Experimental Medicine, 1992, vol. 176, pp. 1453–1457.*
Verma et al (Nature, 1997, vol. 389, pp. 239–242).*
Eck et al Gene–Based Therapy, In: The Pharmacological Basis of Therapeutics, Goodman and Gilman, Ed.s, 1996, pp. 77–10.*
Orkin et al ("Report and Recommendation of the Panel to Assess the NIH Investment in Research on Gene Therapy", NIH, 1995).*
Brock, Biology of Microorganisms, 1979, p. 547, lines 31–35.*
Seo et al, "Factors that influence the mutagenic patterns of DNA adducts from chemical carcinogens", Mutation Research, 2000, vol. 463, pp. 215–246.*
Hruszkewycz et al, "Bypass of a hydrocarbon adduct in an oligonucleotide template mediated by mispairing adjacent to the adduct", Carcinogenesis, 1991, vol. 12, pp. 2185–2187.*
Paul, W.E., ed., Fundamental Immunology (Textbook), 1993, 3rd edition, pp. 249–251.*
Accession No. C03267, Oct. 6, 2000.*
Accession No. AF117106, Jan. 26, 1999.*
Alberts et al, Ed., Molecular Biology of the Cell (textbook), 1996, 3rd edition, p. 465.*
Shantz and Pegg, "Translational regulation of ornithine decarboxylase and other enzymes", International J of Biochemistry and Cell Biology, 1999, vol. 31, pp. 107–122.*
McClean and Hill, "Evidence of post–translational regulation of p–glycoprotein", European J. of Cancer, 1993, vol. 29A, pp. 2243–2248.*
Fu et al, "Translational regulation of human p53 gene expression", EMBO, 1996, vol. 15, pp. 4392–4401.*
Abbas et al, Cellular and Molecular Immunology (textbook), 1991, "General Properties of Immunologic tolerance", pp. 207–208.*
Chen, et al. "Identification of multiple cancer/testis antigens by allogeneic antibody screening of a melanomaa cell library." Proc. Natl. Acad. Sci USA 95: 6919–6923 (6/98).
Lucas, et al., "Identification of a new MAGE Gene with Tumor–specific Expression by Representional Difference Analysis." Canc. Res. 58: 743–752 (1998).

* cited by examiner

*Primary Examiner*—Karen A. Canella
(74) *Attorney, Agent, or Firm*—Fulbright & Jaworski LLP

(57) ABSTRACT

The invention relates to newly identified cancer associated antigens, referred to as CT7, KOC-2 and KOC-3. The invention also relates to observations regarding known molecule KOC-1. It has been discovered that each of these molecules provokes antibodies when expressed by a subject. The ramifications of this observation are also a part of this invention.

20 Claims, No Drawings

ISOLATED NUCLEIC ACID MOLECULE ENCODING CANCER ASSOCIATED ANTIGENS, THE ANTIGENS PER SE, AND USES THEREOF

RELATED APPLICATION

This application is a continuation in part of Ser. No. 09/061,709 filed Apr. 17, 1998, now U.S. Pat. No. 6,297,364, incorporated by reference.

FIELD OF THE INVENTION

This invention relates to antigens associated with cancer, the nucleic acid molecules encoding them, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

This methodology has been applied to a range of tumor types, including those described by Sahin et al., supra, and Pfreandschuh, supra, as well as to esophageal cancer (Chen et al., Proc. Natl. Acad. Sci. USA 94: 1914–1918 (1997)); lung cancer (Güre et al., Cancer Res. 58: 1034–1041 (1998)); colon cancer (Ser. No. 08/948,705 filed Oct. 10, 1997) incorporated by reference, and so forth. Among the antigens identified via SEREX are the SSX2 molecule (Sahin et al., Proc. Natl. Acad. Sci. USA 92: 11810–11813 (1995); Tureci et al., Cancer Res. 56: 4766–4772 (1996); NY-ESO-1 Chen, et al., Proc. Natl. Acad. Sci. USA 94: 1914–1918 (1997); and SCP1 (Ser. No. 08/892,705 filed Jul. 15, 1997) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. The inventors have modified standard SEREX protocols and have screened a cell line known to be a good source of the antigens listed supra, using allogeneic patient sample. New antigens have been identified in this way and have been studied. Also, a previously known molecule has now been identified via SEREX techniques.

DETAILED DESCRIPTION OF PREFERRED EMBODIMENTS

EXAMPLE 1

The melanoma cell referred to as SK-MEL-37 was used, because it has been shown to express a number of members of the CT antigen family, including MAGE-1 (Chen et al., Proc. Natl. Acad. Sci. USA 91: 1004–1008(1994); NY-ESO-1 (Chen et al. Proc. Natl. Acad. Sci. USA 94: 1914–1918 (1997)); and various members of the SSX family (Gure et al., Int. J. Cancer 72: 965–971 (1997)).

Total RNA was extracted from cultured samples of SK-MEL-37 using standard methods, and this was then used to construct a cDNA library in commercially available, λZAP expression vector, following protocols provided by the manufacturer. The cDNA was then transfected into *E. coli* and screened, following Sahin et al., Proc. Natl. Acad. Sci. USA 92: 11810–11813 (1995), incorporated by reference, and Pfreundschuh, U.S. Pat. No. 5,698,396, also incorporated by reference. The screening was done with allogeneic patient serum "NW38." This serum had been shown, previously, to contain high titer antibodies against MAGE-1 and NY-ESO-1. See, e.g., Jäger et al., J. Exp. Med. 187: 265–270 (1998), incorporated by reference. In brief, serum was diluted 1:10, preabsorbed with lysates of transfected *E. coli,* further diluted to 1:2000, and then incubated overnight at room temperature with nitrocellulose membranes containing phage plaques, prepared in accordance with Sahin et al., and Pfreundschuh, supra. The library contained total of $2.3 \times 10^7$ primary clones. After washing, the filters were incubated with alkaline phosphatase conjugated, goat anti-human Fcγ secondary antibodies, and were then visualized by incubating with 5-bromo-4-chloro-3-indolyl phosphate, and nitroblue tetrazolium.

After screening $1.5 \times 10^5$ of the clones, a total of sixty-one positives had been identified. Given this number, screening was stopped, and the positive clones were subjected to further analysis.

EXAMPLE 2

The positive clones identified in example 1, supra, were purified, the inserts were excised in vitro, and inserted into a commercially available plasmid, pBK-CMV, and then evaluated on the basis of restriction mapping with EcoRI and XbaI. Clones which represented different inserts on the basis of this step were sequenced, using standard methodologies.

There was a group of 10 clones, which could not be classified other than as "miscellaneous genes", in that they did not seem to belong to any particular family. They consisted of 9 distinct genes, of which four were known, and five were new. The fifty one remaining clones were classified into four groups. The data are presented in Tables 1 and 2, which follow.

The largest group are genes related to KOC ("KH-domain containing gene, overexpressed in cancer" which has been shown to be overexpressed in pancreatic cancer, and maps to chromosome 7p11.5. See Mueller-Pillasch et al., Oncogene 14: 2729–2733 (1997). Two of the 33 were derived from the KOC gene, and the other 31 were derived from two previously unidentified, but related genes. Examples 6 et seq. describe work on this group of clones.

Eleven clones, i.e., Group 2, were MAGE sequences. Four were derived from MAGE-4a, taught by DePlaen et al., Immunogenetics 40: 360–369, Genbank U10687, while the other 7 hybridized to a MAGE-4a probe, derived from the 5' sequence, suggesting they belong to the MAGE family.

The third group consisted of five clones of the NY-ESO-1 family. Two were identical to the gene described by Chen et al., Proc. Natl. Acad. Sci. USA 94: 1914–1918 (1997), and in Ser. No. 08/725,182, filed Oct. 3, 1996, incorporated by reference. The other three were derived from a second member of the NY-ESO-1 family, i.e., LAGE-1. See U.S. application Ser. No. 08/791,495, filed Jan. 27, 1997 and incorporated by reference.

The fourth, and final group, related to a novel gene referred to as CT7. This gene, the sequence of which is presented as SEQ ID NO: 1, was studied further.

TABLE 1

SEREX-identified genes from allogeneic screening of SK-MEL-37 library

| Gene group | # of clones | Comments |
| --- | --- | --- |
| KOC | 33 | derived from 3 related genes |
| MAGE | 11 | predominantly MAGE-4a (see text) |
| NY-ESO-1 | 5 | derived from 2 related genes (NY-ESO-1, LAGE-1) |
| CT7 | 2 | new cancer/testis antigen |
| Miscellaneous | 10 | sec Table 2 |

TABLE 2

SEREX-identified genes from allogeneic screening of SK-MEL-37 library--Miscellaneous group

| Clone designation | Gene |
| --- | --- |
| MNW-4, MNW-7 | S-adenyl homocysteine hydrolase |
| MNE-6a | Glutathione synthetase |
| MNW-24 | proliferation-associated protein p38-2G4 |
| MNW-27a | phosphoribosyl pyrophosphate synthetase-associated protein 39 |
| MNW-6b | unknown gene, identical to sequence tags from pancreas, uterus etc. |
| MNW-14b | unknown gene, identical to sequence tags from lung, brain, fibroblast etc. |
| MNW-34a | unknown gene, identical to sequence tags from multiple tissues |
| MNW-17 | unknown gene, identical to sequence tags from pancreas and fetus |
| MNW-29a | unknown gene, no significant sequence homology, universally expressed |

EXAMPLE 3

The two clones for CT7, referred to supra, were 2184 and 1965 base pairs long. Analysis of the longer one was carried out. It presented an open reading frame of 543 amino acids, which extended to the 5' end of the sequence, indicating that it was a partial cDNA clone.

In order to identify the complete sequence, and to try to identify additional, related genes, a human testicular cDNA library was prepared, following standard methods, and screened with probes derived from the longer sequence, following standard methods.

Eleven positives were detected, and sequenced, and it was found that all derived from the same gene. When the polyA tail was excluded, full length transcript, as per SEQ ID NO: 1, consisted of 4265 nucleotides, broken down into 286 base pairs of untranslated 5'-region, a coding region of 3429 base pairs, and 550 base pairs of untranslated 3' region. The predicted protein is 1142 amino acids long, and has a calculated molecular mass of about 125 kilodaltons. See SEQ ID NO: 2.

The nucleotide and deduced amino acid sequences were screened against known databases, and there was some homology with the MAGE-10 gene, described by DePlaen et al., Immunogenetics 40: 360–369(1994). The homology was limited to about210 carboxy terminal amino acids, i.e., amino acids 908–1115 of the subject sequence, and 134–342 of MAGE-10. The percent homology was 56%, rising to 75% when conservative changes are included.

There was also extensive homology with a sequence reported by Lucas et al., Canc. Res. 58: 743–752 (1998), and application Ser. No. 08/845,528 filed Apr. 25, 1997, also incorporated by reference. A total of 14 nucleotides differ in the open reading fine, resulting in a total of 11 amino acids which differ between the sequences.

The 5' region of the nucleotide and sequence and corresponding amino acid sequence demonstrates a strikingly repetitive pattern, with repeats rich in serine, proline, glutamine, and leucine, with an almost invariable core of PQSPLQI (SEQ ID NO: 3). In the middle of the molecule, 11 almost exact repeats of 35 amino acids were observed. The repetitive portions make up about 70% of the entire sequence, begin shortly after translation initiation, at position 15, and ending shortly before the region homologous to MAGE 4a.

EXAMPLE 4

The expression pattern for mRNA of CT7 was then studied, in both normal and malignant tissues. RT-PCR was used, employing primers specific for the gene. The estimated melting temperature of the primers was 65–70° C., and they were designed to amplify 300–600 base pair segments. A total of 35 amplification cycles were carried out, at an annealing temperature of 60° C. Table 3, which follows, presents the data for human tumor tissues. CT7 was expressed in a number of different samples. Of fourteen normal tissues tested, there was strong expression in testis, and none in colon, brain, adrenal, lung, breast, pancreas, prostate, thymus or uterus tissue. There was low level expression in liver, kidney, placenta and fetal brain, with fetal brain sowing three transcripts of different size. The level of expression was at least 20–50 times lower than in testis. Melanoma cell lines were also screened. Of these 7 of the 12 tested showed strong expression, and one showed weak expression.

Table 3. CT7 mRNA Expression in Various Humor Tumors by RT-PCR

| Tumor type | mRNA, positive/total |
| --- | --- |
| Melanoma | 7/10 |
| Breast cancer | 3/10 |
| Lung cancer | 3/9 |
| Head/neck cancer | 5/14 |
| Bladder cancer | 4/9 |
| Colon cancer | 1/10 |
| Leimyosarcoma | 1/4 |
| synovial sarcoma | 2/4 |
| Total | 26/70 |

EXAMPLE 5

Southern blotting experiments were then carried out to determine if CT7 belonged to a family of genes. In these experiments, genomic DNA was extracted from normal human tissues. It was digested with BamHI, EcoRI, and HindIII, separated on a 0.7% agarose gel, blotted onto a nitrocellulose filter, and hybridized, at high stringency (65° C., aqueous buffer), with a $^{32}$P labelled probe, derived from SEQ ID NO: 1.

The blotting showed anywhere from two to four bands, suggesting one or two genes in the family.

EXAMPLE 6

As noted in example 2, surra, thirty three of the sixty one positive clones were related to KOC. Clones were sequenced using standard methodologies. As indicated supra, one clone was identical to KOC, initially reported by Müeller-Pillasch, et al., supra. Given that two additional related sequences were identified, the known KOC gene is referred to as KOC-1 hereafter (SEQ ID NO: 4). The second clone, referred to as KOC-2 hereafter, was found once. The sequence is presented as SEQ ID NO: 5. Its deduced amino acid sequence is 72.5% identical to that for KOC-1.

The third sequence, KOC-3, appeared thirty times (SEQ ID NO: 6). Its deduced amino acid sequence is 63% identical to KOC-1.

Testicular cDNA libraries were analyzed in the same way that the SK-MEL-37 library was analyzed, i.e., with allogeneic serum from NW-38. See example 3, supra.

Following analysis of testicular libraries, a longer form of KOC-2 was isolated. This is presented as SEQ ID NO: 7. When SEQ ID NOS: 5 & 7 are compared, the former is 1705 base pairs in length, without a polyA tail. It contains 1362 base pairs of coding sequence, and 343 base pairs of 3' untranslated sequence. Nucleotides 275–1942 of SEQ ID NO: 7 are identical to nucleotides 38–1705 of SEQ ID NO: 5.

The sequence of KOC-3, set forth as SEQ ID NO: 6, is 3412 base pairs long, and consists of 72 base pairs of 5' untranslated region, 1707 base pairs of open reading frame, and 1543 base pairs of untranslated, 3' region. An alternate form was also isolated, (SEQ ID NO: 8), and is 129 base pairs shorter than SEQ ID NO: 6.

EXAMPLE 7

Expression patterns for KOC-1, KOC-2 and KOC-3 were then studied, using RT-PCR and the following primer pairs:

GAAAGTATCT TCAAGGACGC C

CTGCAAGGGG TTTTGCTGGG CG  (SEQ ID NOS: 9 & 10).

TCCTTGCGCG CTGCGGCCTC AG

CCAACTGGTG GCCATRCAGCT TC  (SEQ ID NOS: 11 & 12)

GCTCTTTGGG GACAGGAAGG TC

GACGTTGACA ACGGCGGTTT CT  (SEQ ID NOS: 13 & 14).

SEQ ID NOS: 9 & 10 were designed to amplify KOC-1 while SEQ ID NOS: 11 & 12 were designed to amplify KOC-2, and SEQ ID NOS: 13 & 14 were designed to amplify KOC-3.

To carry out the RT-PCR, relevant primer pairs were added to cDNA samples prepared from various mRNAs by reverse transcription. PCR was then carried out at an annealing temperature of 60° C., and extension at 72° C., for 35 cycles. The resulting products were then analyzed by gel electrophoresis.

SEQ ID NOS 9 & 10 amplify nucleotides 305–748 of SEQ ID NO: 1. A variety of normal and malignant cell types were tested. Strong expression was found in testis, moderate expression in normal brain, and low levels of expression were found in normal colon, kidney, and liver.

The Müeller-Pillasch paper, cited supra, identified expression of KOC-1 in pancreatic tumor cell lines, gastric cancer, and normal placenta, via Northern blotting. This paper also reported that normal heart, brain, lung, liver, kidney and pancreatic tissue were negative for KOC-1 expression. The difference in results suggests that the level of expression of KOC-1 is very low in normal tissues.

When KOC-2 expression was studied, the only positive normal tissue was testis (brain, liver, kidney and colon were negative).

Modification of the protocol for detecting KOC-2 resulted in positives in normal kidney, liver and melanoma.

When KOC-3 expression was studied, it was found that the gene was universally expressed in normal tissues, with highest expression in testis.

The pattern of expression of KOC-3 in different melanoma cell lines was analyzed, using standard Northern blotting. Over expression in several cell lines was observed, which is consistent with the more frequent isolation of this clone than any other.

EXAMPLE 8

A study was carried out to determine if KOC-1 is expressed at higher levels in melanoma cells, as compared to normal skin cells. This was done using representational difference analysis, or "RDA." See Lisitsyn, et al. Science 259: 946–951 (1993), and O'Neill, et al. Nucl. Acids Res. 25:2681–2 (1997), both of which are incorporated by reference. Specifically, tester cDNA was taken from SK-MEL-37, and driver cDNA was taken from a skin sample representing mRNA from various cell types in the skin. The cDNAs were digested with either Tsp509I, Hsp92II, or DpnII. When DpnII was the enzyme used for digestion, adaptor oligonucleotides R-Bgl-24, J-Bgl-24, and N-Bgl-24 described by O'Neill, et al., supra, and Hubank, et al. Nucl. Acids Res. 22:5640–5648 (1994) were used. When Tsp509I was the endonuclease, the same adaptors were used, as were R-Tsp-12, i.e.:

AATTTGCGGT GA                    (SEQ ID NO: 15)

J-Tsp-12, i.e.:

AATTTGTTCA TG                    (SEQ ID NO: 16)

and N-Tsp-12, i.e.:

AATTTTCCCT CG                    (SEQ ID NO: 17)

When Hsp92II was the endonuclease, the adaptors were:

R-Hsp-24, i.e.:

AGCACTCTCC AGCCTCTCAC CATG        (SEQ ID NO: 18);

J-Hsp-24, i.e.:

ACCGACGTCG ACTATCATG CATG         (SEQ ID NO: 19);

N-Hsp-24, i.e.:

AGGCAACTGT GCTATCCGAG CATG        (SEQ ID NO: 20);

R-Hsp-8, i.e.:

GTGAGAGG                            (SEQ ID NO: 21);

J-Hsp-8, i.e.:

CATGGATG                            (SEQ ID NO: 22);

N-Hsp-8, i.e.:

CTCGGATA                            (SEQ ID NO: 23).

In order to hybridize tester and driver, either 3×EE buffer (30 mM EPPS, pH8, 3 mM EDTA), or a buffer of 2.4M tetraethylammonium chloride (TEACl) 3 mM EDTA, 10 mM Tris HC1, pH8, was used. When DNA was dissolved in 10 µl of TEACl buffer, it was denatured at 80° C. for 10 minutes, followed by renaturing at 42° C. for 20 hours. Amplicons were gel purified, and the DP3 or DP2 product was ligated into BamHI (when DpnII was used), EcoRI (when Tsp 509I was used), or SpHI (when Hsp92II was used), cloning vectors were digested, and then sequenced. Sequence analysis of the cDNA molecules derived from these experiments identified KOC-1 as one of the genes isolated, indicating that KOC-1 mRNA is present at a higher level in Sk-Mel 37 cells as compared to normal skin cells.

The foregoing examples describe the isolation of a nucleic acid molecule which encodes a cancer associated antigen. "Associated" is used herein because while it is clear that the relevant molecule was expressed by several types of cancer, other cancers, not screened herein, may also express the antigen.

The invention relates to those nucleic acid molecules which encode the antigens CT7, KOC-2 and KOC-3, as described herein, such as a nucleic acid molecule consisting of the nucleotide sequence SEQ ID NO: 1, molecules comprising the nucleotide sequence of SEQ ID NO: 5, 6, 7 or 8 and so forth. Also embraced are those molecules which are not identical to SEQ ID NOS: 1, 5, 6, 7 or 8, but which encode the same antigen.

Also a part of the invention are expression vectors which incorporate the nucleic acid molecules of the invention, in operable linkage (i.e., "operably linked") to a promoter. Construction of such vectors, such as viral (e.g., adenovirus or Vaccinia virus) or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention are the antigens described herein, both in original form and in any different post translational modified forms. The molecules are large enough to be antigenic without any posttranslational modification, and hence are useful as immunogens, when combined with an adjuvant (or without it), in both precursor and post-translationally modified forms. Antibodies produced using these antigens, both poly and monoclonal, are also a part of the invention as well as hybridomas which make monoclonal antibodies to the antigens. The whole protein can be used therapeutically, or in portions, as discussed infra. Also a part of the invention are antibodies against this antigen, be these polyclonal, monoclonal, reactive fragments, such as Fab, (F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. So, too, could one assay for the expression of any of the antigens via any of the standard nucleic acid hybridization assays which are well known to the art, and need not be elaborated upon herein. One could assay for antibodies against the subject molecules, using standard immunoassays as well.

Analysis of SEQ ID NO: 1, 5, 6, 7 and 8 will show that there are 5' and 3' non-coding regions presented therein. The invention relates to those isolated nucleic acid molecules which contain at least the coding segment, i.e., nucleotides 54–593, of SEQ ID NO: 1, nucleotides 1–1019 of SEQ ID NO: 3, nucleotides 73–1780 of SEQ ID NO: 8, and so forth, and which may contain any or all of the non-coding 5' and 3' portions.

Also a part of the invention are portions of the relevant nucleic acid molecules which can be used, for example, as oligonucleotide primers and/or probes, such as one or more of SEQ ID NOS: 7, 8, 9, 10, 11, 12, 13 or 14 as well as amplification product like nucleic acid molecules comprising at least nucleotides 305–748 of SEQ ID NO: 1.

As was discussed supr. % study of other members of the "CT" family reveals that these are also processed to peptides which provoke lysis by cytolytic T cells. There has been a great deal of work on motifs for various MHC or HLA molecules, which is applicable here. Hence, a further aspect of the invention is a therapeutic method, wherein one or more peptides derived from the antigens of the invention which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Similarly, the invention contemplates therapies wherein nucleic acid molecules which encode the proteins of the invention, one or more or peptides which are derived from these proteins are incorporated into a vector, such as a Vaccinia or adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of these antigens simply by monitoring levels of the protein, its expression, antibodies against it and so forth using any or all of the methods set forth supra.

It should be clear that these methodologies may also be used to track the efficacy of a therapeutic regime. Essentially, one can take a baseline value for a protein of interest using any of the assays discussed supra, administer a given therapeutic agent, and then monitor levels of the protein thereafter, observing changes in antigen levels as indicia of the efficacy of the regime.

As was indicated supra, the invention involves, inter alia, the recognition of an "integrated" immune response to the molecules of the invention. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine; and vice versa. Hence, a further aspect of the invention is a method for monitoring efficacy of a vaccine, following administration thereof, by determining levels of antibodies in the subject which are specific for the vaccine itself, or a large molecule of which the vaccine is a part.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of one or more of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Also a part of the inventions are Peptides, such as those set forth in FIG. 1, and those which have as a core sequence

PQSPLQI                    (SEQ ID NO.: 3)

These peptides may be used therapeutically, via administration to a patient who expresses CT7 in connection with a pathology, as well as diagnostically, i.e., to determine if relevant antibodies are present and so forth.

Other features and applications of the invention will be clear to the skilled artisan, and need not be set forth herein. The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated nucleic acid molecule which encodes the protein encoded by the nucleotide sequence set forth at SEQ ID NO: 5, 6, 7 or 8.

2. The isolated nucleic acid molecule of claim 1, selected from the group consisting of the nucleic acid molecule comprising the nucleotide sequence of SEQ ID NO: 5, 6, 7 and 8.

3. An isolated expression vector comprising the isolated nucleic acid molecule of claim 1, operably linked to a promoter.

4. An isolated expression vector comprising the isolated nucleic acid molecule of claim 2, operably linked to a promoter.

5. An isolated recombinant cell comprising the isolated expression vector of claim 3.

6. An isolated recombinant cell comprising the isolated expression vector of claim 4.

7. An isolated recombinant cell comprising the isolated nucleic acid molecule of claim 1.

8. An isolated recombinant cell comprising the isolated nucleic acid molecule of claim 2.

9. The isolated recombinant cell of claim 5, 6, 7 or 8, wherein said recombinant cell is a eukaryotic cell.

10. The isolated nucleic acid molecule of claim 1, which encodes the protein encoded by SEQ ID NO: 5.

11. The isolated nucleic acid molecule of claim 1, which encodes the protein encoded by SEQ ID NO: 6.

12. The isolated nucleic acid molecule of claim 1, which encodes the protein encoded by SEQ ID NO: 8.

13. The isolated nucleic acid molecule of claim 1, comprising SEQ ID NO: 5.

14. The isolated nucleic acid molecule of claim 1, comprising SEQ ID NO: 6.

15. The isolated nucleic acid molecule of claim 1, comprising SEQ ID NO: 7.

16. The isolated nucleic acid molecule of claim 1, comprising SEQ ID NO: 8.

17. The isolated nucleic acid molecule of claim 1, consisting of SEQ ID NO: 7.

18. An isolated nucleic acid molecule consisting of a nucleotide sequence as set forth in SEQ ID NO: 9, 10, 11, 12, 13, or 14.

19. Kit useful in determining expression of a cancer associated antigen, comprising (i) nucleic acid molecules consisting of the nucleotide sequences set forth in SEQ ID NOS: 9 and 10, (ii) nucleic acid molecules consisting of the nucleotide sequences set forth in SEQ ID NOS: 11 and 12, and (iii) nucleic acid molecules consisting of the nucleotide sequences set forth in SEQ ID NOS: 13 and 14, wherein (i), (ii) and (iii) are presented in separate container means in said kit.

20. A composition comprising an isolated expression vector, wherein said isolated expression vector encodes a peptide, wherein said peptide consists of 8 to 25 amino acids which are present in consecutive order in the protein encoded by the isolated nucleic acid molecule of claim 1, and a pharmaceutically acceptable carrier.

* * * * *

SEQUENCE LISTING

<160> NUMBER OF SEQ ID NOS: 23

<210> SEQ ID NO 1
<211> LENGTH: 4265
<212> TYPE: DNA
<213> ORGANISM: Homo sapiens
<220> FEATURE:

<400> SEQUENCE: 1

| | | | | | |
|---|---|---|---|---|---|
| gtctgaagga | cctgaggcat | tttgtgacga | ggatcgtctc | aggtcagcgg | agggaggaga | 60 |
| cttatagacc | tatccagtct | tcaaggtgct | ccagaaagca | ggagttgaag | acctgggtgt | 120 |
| gagggacaca | tacatcctaa | aagcaccaca | gcagaggagg | cccaggcagt | gccaggagtc | 180 |
| aaggttccca | gaagacaaac | cccctaggaa | gacaggcgac | ctgtgaggcc | ctagagcacc | 240 |
| accttaagag | aagaagagct | gtaagccggc | ctttgtcaga | gccatcatgg | gggacaagga | 300 |
| tatgcctact | gctgggatgc | cgagtcttct | ccagagttcc | tctgagagtc | ctcagagttg | 360 |
| tcctgagggg | gaggactccc | agtctcctct | ccagattccc | cagagttctc | ctgagagcga | 420 |
| cgacaccctg | tatcctctcc | agagtcctca | gagtcgttct | gagggggagg | actcctcgga | 480 |
| tcctctccag | agacctcctg | aggggaagga | ctcccagtct | cctctccaga | ttccccagag | 540 |
| ttctcctgag | ggcgacgaca | cccagtctcc | tctccagaat | tctcagagtt | ctcctgaggg | 600 |
| gaaggactcc | ctgtctcctc | tagagatttc | tcagagccct | cctgagggtg | aggatgtcca | 660 |
| gtctcctctg | cagaatcctg | cgagttcctt | cttctcctct | gctttattga | gtattttcca | 720 |
| gagttcccct | gagagtattc | aaagtccttt | tgagggtttt | ccccagtctg | ttctccagat | 780 |
| tcctgtgagc | gccgcctcct | cctccacttt | agtgagtatt | ttccagagtt | ccctgagag | 840 |
| tactcaaagt | ccttttgagg | gttttcccca | gtctccactc | cagattcctg | tgagccgctc | 900 |
| cttctcctcc | actttattga | gtattttcca | gagttcccct | gagagaagtc | agagaacttc | 960 |
| tgagggtttt | gcacagtctc | ctctccagat | tcctgtgagc | tcctcctcgt | cctccacttt | 1020 |
| actgagtctt | ttccagagtt | cccctgagag | aactcagagt | acttttgagg | gttttcccca | 1080 |
| gtctccactc | cagattcctg | tgagccgctc | cttctcctcc | actttattga | gtattttcca | 1140 |
| gagttcccct | gagagaactc | agagtacttt | tgagggtttt | gcccagtctc | ctctccagat | 1200 |
| tcctgtgagc | ccctccttct | cctccacttt | agtgagtatt | ttccagagtt | ccctgagag | 1260 |
| aactcagagt | acttttgagg | gttttcccca | gtctcctctc | cagattcctg | tgagctcctc | 1320 |
| cttctcctcc | actttattga | gtcttttcca | gagttcccct | gagagaactc | agagtacttt | 1380 |
| tgagggtttt | ccccagtctc | ctctccagat | tcctggaagc | ccctccttct | cctccacttt | 1440 |
| actgagtctt | ttccagagtt | cccctgagag | aactcacagt | acttttgagg | gttttcccca | 1500 |
| gtctcctctc | cagattccta | tgacctcctc | cttctcctct | actttattga | gtattttaca | 1560 |
| gagttctcct | gagagtgctc | aaagtgcttt | tgagggtttt | ccccagtctc | ctctccagat | 1620 |
| tcctgtgagc | tcctctttct | cctacacttt | attgagtctt | ttccagagtt | cccctgagag | 1680 |
| aactcacagt | acttttgagg | gttttcccca | gtctcctctc | cagattcctg | tgagctcctc | 1740 |
| ctcctcctcc | tccactttat | tgagtctttt | ccagagttcc | cctgagtgta | ctcaaagtac | 1800 |
| ttttgagggt | tttccccagt | ctcctctcca | gattcctcag | agtcctcctg | aaggggagaa | 1860 |
| tacccattct | cctctccaga | ttgttccaag | tcttcctgag | tgggaggact | ccctgtctcc | 1920 |
| tcactacttt | cctcagagcc | ctcctcaggg | ggaggactcc | ctatctcctc | actactttcc | 1980 |

-continued

```
tcagagccct cctcagggggg aggactccct gtctcctcac tactttcctc agagccctca    2040
gggggaggac tccctgtctc ctcactactt tcctcagagc cctcctcagg gggaggactc    2100
catgtctcct ctctactttc ctcagagtcc tcttcagggg gaggaattcc agtcttctct    2160
ccagagccct gtgagcatct gctcctcctc cactccatcc agtcttcccc agagtttccc    2220
tgagagttct cagagtcctc ctgagggggcc tgtccagtct cctctccata gtcctcagag    2280
ccctcctgag gggatgcact cccaatctcc tctccagagt cctgagagtg ctcctgaggg    2340
ggaggattcc ctgtctcctc tccaaattcc tcagagtcct cttgagggag aggactccct    2400
gtcttctctc catttcctc agagtcctcc tgagtgggag actccctct ctcctctcca    2460
ctttcctcag tttcctcctc aggggagga cttccagtct tctctccaga gtcctgtgag    2520
tatctgctcc tcctccactt ctttgagtct tccccagagt ttccctgaga gtcctcagag    2580
tcctcctgag gggcctgctc agtctcctct ccagagacct gtcagctcct tcttctccta    2640
cactttagcg agtcttctcc aaagttccca tgagagtcct cagagtcctc ctgagggggcc    2700
tgcccagtct cctctccaga gtcctgtgag ctccttcccc tcctccactt catcgagtct    2760
ttcccagagt tctcctgtga gctccttccc ctcctccact tcatcgagtc tttccaagag    2820
ttccccctgag agtcctctcc agagtcctgt gatctccttc tcctcctcca cttcattgag    2880
cccattcagt gaagagtcca gcagcccagt agatgaatat acaagttcct cagacacctt    2940
gctagagagt gattccttga cagacagcga gtccttgata gagagcgagc ccttgttcac    3000
ttatacactg gatgaaaaagg tggacgagtt ggcgcggttt cttctcctca aatatcaagt    3060
gaagcagcct atcacaaagg cagagatgct gacgaatgtc atcagcaggt acacgggcta    3120
ctttcctgtg atcttcagga aagcccgtga gttcatagag atactttttg gcatttccct    3180
gagagaagtg gaccctgatg actcctatgt ctttgtaaac acattagacc tcacctctga    3240
ggggtgtctg agtgatgagc agggcatgtc ccagaaccgc ctcctgattc ttattctgag    3300
tatcatcttc ataaagggca cctatgcctc tgaggaggtc atctgggatg tgctgagtgg    3360
aatagggtg cgtgctggga gggagcactt tgcctttggg gagcccaggg agctcctcac    3420
taaagtttgg gtgcaggaac attacctaga gtaccgggag gtgcccaact cttctcctcc    3480
tcgttacgaa ttcctgtggg gtccaagagc tcattcagaa gtcattaaga ggaaagtagt    3540
agagttttg gccatgctaa agaataccgt ccctattacc tttccatcct cttacaagga    3600
tgctttgaaa gatgtggaag agagagccca ggccataatt gacaccacag atgattcgac    3660
tgccacagaa agtgcaagct ccagtgtcat gtcccccagc ttctcttctg agtgaagtct    3720
agggcagatt cttccctctg agtttgaagg gggcagtcga gtttctacgt ggtggagggc    3780
ctggttgagg ctggagagaa cacagtgcta tttgcatttc tgttccatat gggtagttat    3840
ggggtttacc tgttttactt tgggtattt ttcaaatgct tttcctatta ataacaggtt    3900
taaatagctt cagaatccta gtttatgcac atgagtcgca catgtattgc tgttttctg    3960
gtttaagagt aacagtttga tattttgtaa aaacaaaaac acccaaac acaccacatt    4020
gggaaaaacct tctgcctcat tttgtgatgt gtcacaggtt aatgtggtgt tactgtagga    4080
atttcttga aactgtgaag gaactctgca gttaaatagt ggaataaagt aaaggattgt    4140
taatgtttgc atttcctcag gtcctttagt ctgttgttct tgaaaactaa agatacatac    4200
ctggtttgct tggcttacgt aagaaagtcg aagaaagtaa actgtaataa ataaaagtgt    4260
cagtg                                                                4265
```

```
<210> SEQ ID NO 2
<211> LENGTH: 1142
<212> TYPE: PRT
<213> ORGANISM: Homo sapiens
<220> FEATURE:

<400> SEQUENCE: 2

Met Gly Asp Lys Asp Met Pro Thr Ala Gly Met Pro Ser Leu Leu Gln
                 5                  10                  15

Ser Ser Ser Glu Ser Pro Gln Ser Cys Pro Glu Gly Glu Asp Ser Gln
             20                  25                  30

Ser Pro Leu Gln Ile Pro Gln Ser Ser Pro Glu Ser Asp Asp Thr Leu
         35                  40                  45

Tyr Pro Leu Gln Ser Pro Gln Ser Arg Ser Glu Gly Glu Asp Ser Ser
     50                  55                  60

Asp Pro Leu Gln Arg Pro Pro Glu Gly Lys Asp Ser Gln Ser Pro Leu
 65                  70                  75                  80

Gln Ile Pro Gln Ser Ser Pro Glu Gly Asp Asp Thr Gln Ser Pro Leu
             85                  90                  95

Gln Asn Ser Gln Ser Ser Pro Glu Gly Lys Asp Ser Leu Ser Pro Leu
            100                 105                 110

Glu Ile Ser Gln Ser Pro Pro Glu Gly Glu Asp Val Gln Ser Pro Leu
        115                 120                 125

Gln Asn Pro Ala Ser Ser Phe Phe Ser Ser Ala Leu Leu Ser Ile Phe
    130                 135                 140

Gln Ser Ser Pro Glu Ser Ile Gln Ser Pro Phe Glu Gly Phe Pro Gln
145                 150                 155                 160

Ser Val Leu Gln Ile Pro Val Ser Ala Ala Ser Ser Ser Thr Leu Val
                165                 170                 175

Ser Ile Phe Gln Ser Ser Pro Glu Ser Thr Gln Ser Pro Phe Glu Gly
            180                 185                 190

Phe Pro Gln Ser Pro Leu Gln Ile Pro Val Ser Arg Ser Phe Ser Ser
        195                 200                 205

Thr Leu Leu Ser Ile Phe Gln Ser Ser Pro Glu Arg Ser Gln Arg Thr
    210                 215                 220

Ser Glu Gly Phe Ala Gln Ser Pro Leu Gln Ile Pro Val Ser Ser Ser
225                 230                 235                 240

Ser Ser Ser Thr Leu Leu Ser Leu Phe Gln Ser Ser Pro Glu Arg Thr
                245                 250                 255

Gln Ser Thr Phe Glu Gly Phe Pro Gln Ser Pro Leu Gln Ile Pro Val
            260                 265                 270

Ser Arg Ser Phe Ser Ser Thr Leu Leu Ser Ile Phe Gln Ser Ser Pro
        275                 280                 285

Glu Arg Thr Gln Ser Thr Phe Glu Gly Phe Ala Gln Ser Pro Leu Gln
    290                 295                 300

Ile Pro Val Ser Pro Ser Phe Ser Ser Thr Leu Val Ser Ile Phe Gln
305                 310                 315                 320

Ser Ser Pro Glu Arg Thr Gln Ser Thr Phe Glu Gly Phe Pro Gln Ser
                325                 330                 335

Pro Leu Gln Ile Pro Val Ser Ser Phe Ser Ser Thr Leu Leu Ser
            340                 345                 350

Leu Phe Gln Ser Ser Pro Glu Arg Thr Gln Ser Thr Phe Glu Gly Phe
        355                 360                 365

Pro Gln Ser Pro Leu Gln Ile Pro Gly Ser Pro Ser Phe Ser Ser Thr
    370                 375                 380
```

-continued

```
Leu Leu Ser Leu Phe Gln Ser Pro Glu Arg Thr His Ser Thr Phe
385                 390                 395                 400

Glu Gly Phe Pro Gln Ser Pro Leu Gln Ile Pro Met Thr Ser Ser Phe
            405                 410                 415

Ser Ser Thr Leu Leu Ser Ile Leu Gln Ser Ser Pro Glu Ser Ala Gln
        420                 425                 430

Ser Ala Phe Glu Gly Phe Pro Gln Ser Pro Leu Gln Ile Pro Val Ser
    435                 440                 445

Ser Ser Phe Ser Tyr Thr Leu Leu Ser Leu Phe Gln Ser Ser Pro Glu
450                 455                 460

Arg Thr His Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
            485                 490                 495

Ser Ser Pro Glu Cys Thr Gln Ser Thr Phe Glu Gly Phe Pro Gln Ser
            500                 505                 510

Pro Leu Gln Ile Pro Gln Ser Pro Glu Gly Glu Asn Thr His Ser
    515                 520                 525

Pro Leu Gln Ile Val Pro Ser Leu Pro Glu Trp Glu Asp Ser Leu Ser
    530                 535                 540

Pro His Tyr Phe Pro Gln Ser Pro Gln Gly Glu Asp Ser Leu Ser
545                 550                 555                 560

Pro His Tyr Phe Pro Gln Ser Pro Gln Gly Glu Asp Ser Leu Ser
            565                 570                 575

Pro His Tyr Phe Pro Gln Ser Pro Gln Gly Glu Asp Ser Leu Ser Pro
            580                 585                 590

His Tyr Phe Pro Gln Ser Pro Pro Gln Gly Glu Asp Ser Met Ser Pro
    595                 600                 605

Leu Tyr Phe Pro Gln Ser Pro Leu Gln Gly Glu Glu Phe Gln Ser Ser
    610                 615                 620

Leu Gln Ser Pro Val Ser Ile Cys Ser Ser Ser Thr Pro Ser Ser Leu
625                 630                 635                 640

Pro Gln Ser Phe Pro Glu Ser Ser Gln Ser Pro Pro Glu Gly Pro Val
            645                 650                 655

Gln Ser Pro Leu His Ser Pro Gln Ser Pro Pro Glu Gly Met His Ser
            660                 665                 670

Gln Ser Pro Leu Gln Ser Pro Glu Ser Ala Pro Glu Gly Glu Asp Ser
            675                 680                 685

Leu Ser Pro Leu Gln Ile Pro Gln Ser Pro Leu Glu Gly Glu Asp Ser
    690                 695                 700

Leu Ser Ser Leu His Phe Pro Gln Ser Pro Pro Glu Trp Glu Asp Ser
705                 710                 715                 720

Leu Ser Pro Leu His Phe Pro Gln Phe Pro Gln Gly Glu Asp Phe
    725                 730                 735

Gln Ser Ser Leu Gln Ser Pro Val Ser Ile Cys Ser Ser Ser Thr Ser
            740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
    770                 775                 780

Tyr Thr Leu Ala Ser Leu Leu Gln Ser Ser His Glu Ser Pro Gln Ser
785                 790                 795                 800
```

```
Pro Pro Glu Gly Pro Ala Gln Ser Pro Leu Gln Ser Pro Val Ser Ser
            805                 810                 815

Phe Pro Ser Ser Thr Ser Ser Leu Ser Gln Ser Ser Pro Val Ser
            820                 825                 830

Ser Phe Pro Ser Ser Thr Ser Ser Leu Ser Lys Ser Ser Pro Glu
            835                 840                 845

Ser Pro Leu Gln Ser Pro Val Ile Ser Phe Ser Ser Thr Ser Leu
850                 855                 860

Ser Pro Phe Ser Glu Glu Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910

Asp Glu Leu Ala Arg Phe Leu Leu Lys Tyr Gln Val Lys Gln Pro
            915                 920                 925

Ile Thr Lys Ala Glu Met Leu Thr Asn Val Ile Ser Arg Tyr Thr Gly
        930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Asp Ser Tyr Val Phe
                965                 970                 975

Val Asn Thr Leu Asp Leu Thr Ser Glu Gly Cys Leu Ser Asp Glu Gln
            980                 985                 990

Gly Met Ser Gln Asn Arg Leu Leu Ile Leu Ile Leu Ser Ile Ile Phe
        995                 1000                1005

Ile Lys Gly Thr Tyr Ala Ser Glu Glu Val Ile Trp Asp Val Leu Ser
        1010                1015                1020

Gly Ile Gly Val Arg Ala Gly Arg Glu His Phe Ala Phe Gly Glu Pro
1025                1030                1035                1040

Arg Glu Leu Leu Thr Lys Val Trp Val Gln Glu His Tyr Leu Glu Tyr
                1045                1050                1055

Arg Glu Val Pro Asn Ser Ser Pro Pro Arg Tyr Glu Phe Leu Trp Gly
            1060                1065                1070

Pro Arg Ala His Ser Glu Val Ile Lys Arg Lys Val Val Glu Phe Leu
        1075                1080                1085

Ala Met Leu Lys Asn Thr Val Pro Ile Thr Phe Pro Ser Ser Tyr Lys
        1090                1095                1100

Asp Ala Leu Lys Asp Val Glu Glu Arg Ala Gln Ala Ile Ile Asp Thr
1105                1110                1115                1120

Thr Asp Asp Ser Thr Ala Thr Glu Ser Ala Ser Ser Ser Val Met Ser
                1125                1130                1135

Pro Ser Phe Ser Ser Glu
            1140

<210> SEQ ID NO 3
<211> LENGTH: 7
<212> TYPE: PRT
<213> ORGANISM: Homo sapiens
<220> FEATURE:

<400> SEQUENCE: 3

Pro Gln Ser Pro Leu Gln Ile
1               5
```

-continued

<210> SEQ ID NO 4
<211> LENGTH: 4159
<212> TYPE: DNA
<213> ORGANISM: Homo sapiens
<220> FEATURE:
<221> NAME/KEY: CDS
<222> LOCATION: 3347,3502,3506,3520,3538,3549,3646,3940,3968,3974,4036,
      4056,4062,4080,4080,4115
<223> OTHER INFORMATION: unsure of nucleotide

<400> SEQUENCE: 4

| | | | | | |
|---|---|---|---|---|---|
| ggtggatgcg | tttgggttgt | agctaggctt | tttcttttct | ttctctttta | aaacacatct | 60 |
| agacaaggaa | aaaacaagcc | tcggatctga | tttttcactc | ctcgttcttg | tgcttggttc | 120 |
| ttactgtgtt | tgtgtatttt | aaaggcgaga | agacgagggg | aacaaaacca | gctggatcca | 180 |
| tccatcaccg | tgggtggttt | taattttcg | tttttctcg | ttattttttt | ttaaacaacc | 240 |
| actcttcaca | atgaacaaac | tgtatatcgg | aaacctcagc | gagaacgccg | cccctcgga | 300 |
| cctagaaagt | atcttcaagg | acgccaagat | cccggtgtcg | ggaccttcc | tggtgaagac | 360 |
| tggctacgcg | ttcgtggact | gcccggacga | gagctgggcc | ctcaaggcca | tcgaggcgct | 420 |
| ttcaggtaaa | atagaactgc | acgggaaacc | catagaagtt | gagcactcgg | tcccaaaaag | 480 |
| gcaaaggatt | cggaaacttc | agatacgaaa | tatcccgcct | catttacagt | gggaggtgct | 540 |
| ggatagttta | ctagtccagt | atggagtggt | ggagagctgt | gagcaagtga | acactgactc | 600 |
| ggaaactgca | gttgtaaatg | taacctattc | cagtaaggac | caagctagac | aagcactaga | 660 |
| caaactgaat | ggatttcagt | tagagaattt | cacctttgaaa | gtagcctata | tccctgatga | 720 |
| aatggccgcc | cagcaaaaacc | ccttgcagca | gccccgaggt | cgccgggggc | ttgggcagag | 780 |
| gggctcctca | aggcagggt | ctccaggatc | cgtatccaag | cagaaaccat | gtgatttgcc | 840 |
| tctgcgcctg | ctggttccca | cccaatttgt | tggagccatc | ataggaaaag | aaggtgccac | 900 |
| cattcggaac | atcaccaaac | agacccagtc | taaaatcgat | gtccaccgta | agaaaatgc | 960 |
| ggggctgct | gagaagtcga | ttactatcct | ctctactcct | gaaggcacct | ctgcggcttg | 1020 |
| taagtctatt | ctggagatta | tgcataagga | agctcaagat | ataaaattca | cagaagagat | 1080 |
| ccccttgaag | attttagctc | ataataactt | tgttggacgt | cttattggta | aagaaggaag | 1140 |
| aaatcttaaa | aaaattgagc | aagacacaga | cactaaaatc | acgatatctc | cattgcagga | 1200 |
| attgacgctg | tataatccag | aacgcactat | tacagttaaa | ggcaatgttg | agacatgtgc | 1260 |
| caaagctgag | gaggagatca | tgaagaaaat | cagggagtct | tatgaaaatg | atattgcttc | 1320 |
| tatgaatctt | caagcacatt | taattcctgg | attaaatctg | aacgccttgg | gtctgttccc | 1380 |
| acccacttca | gggatgccac | ctcccacctc | agggcccct | tcagccatga | ctcctcccta | 1440 |
| cccgcagttt | gagcaatcag | aaacggagac | tgttcatcag | tttatcccag | ctctatcagt | 1500 |
| cggtgccatc | atcggcaagc | agggccagca | catcaagcag | ctttctcgct | tgctggagc | 1560 |
| ttcaattaag | attgctccag | cggaagcacc | agatgctaaa | gtgaggatgg | tgattatcac | 1620 |
| tggaccacca | gaggctcagt | tcaaggctca | gggaagaatt | tatggaaaaa | ttaaagaaga | 1680 |
| aaactttgtt | agtcctaaag | aagaggtgaa | acttgaagct | catatcagag | tgccatcctt | 1740 |
| tgctgctggc | agagttattg | gaaaaggagg | caaaacggtg | aatgaacttc | agaatttgtc | 1800 |
| aagtgcagaa | gttgttgtcc | ctcgtgacca | gacacctgat | gagaatgacc | aagtggttgt | 1860 |
| caaaataact | ggtcacttct | atgcttgcca | ggttgcccag | agaaaaattc | aggaaattct | 1920 |
| gactcaggta | aagcagcacc | aacaacagaa | ggctctgcaa | agtggaccac | ctcagtcaag | 1980 |
| acggaagtaa | aggctcagga | aacagcccac | cacagaggca | gatgccaaac | caaagacaga | 2040 |

-continued

```
ttgcttaacc aacagatggg cgctgacccc ctatccagaa tcacatgcac aagttttta     2100
ctagccagtt gtttctgagg accaggcaac ttttgaactc ctgtctctgt gagaatgtat    2160
actttatgct ctctgaaatg tatgacaccc agctttaaaa caaacaaaca aacaaacaaa    2220
aaaagggtgg gggagggagg gaaagagaag agctctgcac ttcccttgt tgtagtctca     2280
cagtataaca gatattctaa ttcttcttaa tattcccca taatgccaga aattggctta    2340
atgatgcttt cactaaattc atcaaataga ttgctcctaa atccaattgt taaaattgga    2400
tcagaataat tatcacagga acttaaatgt taagccatta gcatagaaaa actgttctca    2460
gttttatttt tacctaacac taacatgagt aacctaaggg aagtgctgaa tggtgttggc    2520
agggtatta aacgtgcatt tttactcaac tacctcaggt attcagtaat acaatgaaaa     2580
gcaaaattgt tccttttttt tgaaaattt atatacttta taatgataga agtccaaccg     2640
ttttttaaaa aataaattta aaatttaaca gcaatcagct aacaggcaaa ttaagatttt    2700
tacttctggc tggtgacagt aaagctgaa aattaatttc agggtttttt gaggcttttg     2760
acacagttat tagttaaatc aaatgttcaa aaatacggag cagtgcctag tatctggaga    2820
gcagcactac catttattct ttcatttata gttgggaaag ttttgacgg tactaacaaa     2880
gtggtcgcag gagattttgg aacggctggt ttaaatggct tcaggagact tcagtttttt    2940
gtttagctac atgattgaat gcataataaa tgctttgtgc ttctgactat caatacctaa    3000
agaaagtgca tcagtgaaga gatgcaagac tttcaactga ctggcaaaaa gcaagcttta    3060
gcttgtctta taggatgctt agtttgccac tacacttcag accaatggga cagtcataga    3120
tggtgtgaca gtgtttaaac gcaacaaaag gctacatttc catggggcca gcactgtcat    3180
gagcctcact aagctatttt gaagattttt aagcactgat aaattaaaaa aaaaaaaaa    3240
aaattagact ccaccttaag tagtaaagta taacaggatt tctgtatact gtgcaatcag    3300
ttctttgaaa aaaagtcaa aagatagaga atacaagaaa agttttnggg atataatttg     3360
aatgactgtg aaaacatatg accttgata acgaactcat ttgctcactc cttgacagca    3420
aagcccagta cgtacaattg tgttgggtgt gggtggtctc caaggccacg ctgctctctg    3480
aattgatttt ttgagttttg gnttgnaaga tgatcacagn catgttacac tgatcttnaa    3540
ggacatatnt tataacccctt taaaaaaaa atcccctgcc tcattcttat ttcgagatga    3600
atttcgatac agactagatg tctttctgaa gatcaattag acattntgaa aatgatttaa    3660
agtgttttcc ttaatgttct ctgaaaacaa gtttcttttg tagttttaac caaaaaagtg    3720
ccctttttgt cactggtttc tcctagcatt catgattttt ttttcacaca atgaattaaa    3780
attgctaaaa tcatggactg gctttctggt tggatttcag gtaagatgtg tttaaggcca    3840
gagcttttct cagtatttga ttttttttccc caatatttga ttttttaaaa atatacacat    3900
aggagctgca tttaaaacct gctggtttaa attctgtcan atttcacttc tagccttta    3960
gtatggcnaa tcanaattta cttttactta agcatttgta atttggagta tctggtacta    4020
gctaagaaat aattcnataa ttgagttttg tactcnccaa anatgggtca ttcctcatgn    4080
ataatgtncc cccaatgcag cttcatttc caganaccttt gacgcaggat aaattttttc    4140
atcatttagg tccccaaaa                                                  4159
```

<210> SEQ ID NO 5
<211> LENGTH: 1708
<212> TYPE: DNA
<213> ORGANISM: Homo sapiens
<220> FEATURE:
<221> NAME/KEY: CDS
<222> LOCATION: 1384,1464,1533,1571,1595
<223> OTHER INFORMATION: unsure of nucleotide

<400> SEQUENCE: 5

| | | | | | |
|---|---|---|---|---|---|
| agggacgctg | ccgcaccgcc | ccagtttacc | ccggggagcc | atcatgaagc | tgaatggcca | 60 |
| ccagttggag | aaccatgccc | tgaaggtctc | ctacatcccc | gatgagcaga | tagcacaggg | 120 |
| acctgagaat | gggcgccgag | ggggcttttgg | ctctcggggt | cagccccgcc | agggctcacc | 180 |
| tgtggcagcg | ggggccccag | ccaagcagca | gcaagtggac | atccccttc | ggctcctggt | 240 |
| gcccacccag | tatgtgggtg | ccattattgg | caaggagggg | gccaccatcc | gcaacatcac | 300 |
| aaaacagacc | cagtccaaga | tagacgtgca | taggaaggag | aacgcaggtg | cagctgaaaa | 360 |
| agccatcagt | gtgcactcca | cccctgaggg | ctgctcctcc | gcttgtaaga | tgatcttgga | 420 |
| gattatgcat | aaagaggcta | aggacaccaa | aacggctgac | gaggttcccc | tgaagatcct | 480 |
| ggcccataat | aactttgtag | ggcgtctcat | tggcaaggaa | ggacggaacc | tgaagaaggt | 540 |
| agagcaagat | accgagacaa | aaatcaccat | ctcctcgttg | caagacctta | ccctttacaa | 600 |
| ccctgagagg | accatcactg | tgaaggggggc | catcgagaat | tgttgcaggg | ccgagcagga | 660 |
| aataatgaag | aaagttcggg | aggcctatga | gaatgatgtg | gctgccatga | gctctcacct | 720 |
| gatccctggc | ctgaacctgg | ctgctgtagg | tcttttccca | gcttcatcca | gcgcagtccc | 780 |
| gccgcctccc | agcagcgtta | ctggggctgc | tccctatagc | tcctttatgc | aggctcccga | 840 |
| gcaggagatg | gtgcaggtgt | ttatccccgc | ccaggcagtg | ggcgccatca | tcggcaagaa | 900 |
| ggggcagcac | atcaaacagc | tctcccggtt | tgccagcgcc | tccatcaaga | ttgcaccacc | 960 |
| cgaaacacct | gactccaaag | ttcgtatggt | tatcatcact | ggaccgccag | aggcccaatt | 1020 |
| caaggctcag | ggaagaatct | atggcaaact | caaggaggaa | aacttctttg | gtcccaagga | 1080 |
| ggaagtgaag | ctggagaccc | acatacgtgt | gccagcatca | gcagctggcc | gggtcattgg | 1140 |
| caaaggtgga | aaaacggtga | acgagttgca | gaatttgacg | gcagctgagg | tggtagtacc | 1200 |
| aagagaccag | accctgatg | agaacgacca | ggtcatcgtg | aaaatcatcg | gacatttcta | 1260 |
| tgccagtcag | atggctcaac | ggaagatccg | agacatcctg | gcccaggtta | agcagcagca | 1320 |
| tcagaaggga | cagagtaacc | aggcccaggc | acggaggaag | tgaccagccc | ctccctgtcc | 1380 |
| cttngagtcc | aggacaacaa | cgggcagaaa | tcgagagtgt | gctctccccg | gcaggcctga | 1440 |
| gaatgagtgg | gaatccggga | cacntgggcc | gggctgtaga | tcaggtttgc | ccacttgatt | 1500 |
| gagaaagatg | ttccagtgag | gaaccctgat | ctntcagccc | caaacaccca | cccaattggc | 1560 |
| ccaacactgt | ntgcccctcg | gggtgtcaga | aattntagcg | caaggcactt | ttaaacgtgg | 1620 |
| attgttttaaa | gaagctctcc | aggccccacc | aagagggtgg | atcacacctc | agtgggaaga | 1680 |
| aaaataaaat | ttccttcagg | ttttaaaa | | | | 1708 |

<210> SEQ ID NO 6
<211> LENGHT: 3412
<212> TYPE: DNA
<213> ORGANISM: Homo sapiens
<220> FEATURE:
<221> NAME/KEY: CDS
<222> LOCATION: 3372
<223> OTHER INFORMATION: unsure of nucleotide

<400> SEQUENCE: 6

| | | | | | |
|---|---|---|---|---|---|
| ggcagcggag | gaggcgagga | gcgccgggta | ccgggccggg | ggagccgcgg | gctctcgggg | 60 |
| aagagacgga | tgatgaacaa | gctttacatc | gggaacctga | gccccgccgt | caccgccgac | 120 |

```
gacctccggc agctctttgg ggacaggaag ctgcccctgg cgggacaggt cctgctgaag      180
tccggctacg ccttcgtgga ctaccccgac cagaactggg ccatccgcgc catcgagacc      240
ctctcgggta aagtggaatt gcatgggaaa atcatggaag ttgattactc agtctctaaa      300
aagctaagga gcaggaaaat tcagattcga acatccctc ctcacctgca gtgggaggtg       360
ttggatggac ttttggctca atatgggaca gtggagaatg tggaacaagt caacacagac      420
acagaaaccg ccgttgtcaa cgtcacatat gcaacaagag aagaagcaaa aatagccatg      480
gagaagctaa gcgggcatca gtttgagaac tactccttca agatttccta catcccggat      540
gaagaggtga gctccccttc gccccctcag cgagcccagc gtggggacca ctcttcccgg      600
gagcaaggcc acgcccctgg gggcacttct caggccagac agattgattt cccgctgcgg      660
atcctggtcc ccacccagtt tgttggtgcc atcatcggaa aggagggctt gaccataaag      720
aacatcacta agcagaccca gtcccgggta gatatccata aaaagagaa ctctggagct       780 gcagagaagc ctgtcaccat ccatgccacc ccagagggga cttctgaagc atgccgcatg      840
attcttgaaa tcatgcagaa agaggcagat gagaccaaac tagccgaaga gattcctctg      900
aaaatcttgg cacacaatgg cttggttgga agactgattg aaaagaagg cagaaatttg       960 aagaaaattg aacatgaaac agggaccaag ataacaatct catctttgca ggatttgagc     1020
atatacaacc cggaaagaac catcactgtg aagggcacag ttgaggcctg tgccagtgct     1080
gagatagaga ttatgaagaa gctgcgtgag gcctttgaaa atgatatgct ggctgttaac     1140
caacaagcca atctgatccc agggttgaac ctcagcgcac ttggcatctt ttcaacagga     1200
ctgtccgtgc tatctccacc agcagggccc cgcggagctc cccccgctgc cccctaccac     1260
cccttcacta cccactccgg atacttctcc agcctgtacc cccatcacca gtttggcccg     1320
ttcccgcatc atcactctta tccagagcag gagattgtga atctcttcat cccaacccag     1380
gctgtgggcg ccatcatcgg gaagaagggg cacacatca aacagctggc gagattcgcc      1440
ggagcctcta tcaagattgc ccctgcggaa ggcccagacg tcagcgaaag gatggtcatc     1500
atcaccgggc caccggaagc ccagttcaag gcccagggac ggatctttgg gaaactgaaa     1560
gaggaaaact tctttaaccc caaagaagaa gtgaagctgg aagcgcatat cagagtgccc     1620
tcttccacag ctggccgggt gattggcaaa ggtggcaaga ccgtgaacga actgcagaac     1680
ttaaccagtg cagaagtcat cgtgcctcgt gaccaaacgc cagatgaaaa tgaggaagtg     1740
atcgtcagaa ttatcgggca cttctttgct agccagactg cacagcgcaa gatcagggaa     1800
attgtacaac aggtgaagca gcaggagcag aaataccctc agggagtcgc ctcacagcgc     1860
agcaagtgag gctcccacag gcaccagcaa acaacggat gaatgtagcc cttccaacac      1920
ctgacagaat gagaccaaac gcagccagcc agatcgggag caaaccaaag accatctgag     1980
gaatgagaag tctgcggagg cggccaggga ctctgccgag gccctgagaa ccccaggggc     2040
cgaggagggg cggggaaggt cagccaggtt tgccagaacc accgagcccc gcctcccgcc     2100
ccccagggct tctgcaggct tcagccatcc acttcaccat ccactcggat ctctcctgaa     2160
ctcccacgac gctatcccc ttagttgaac taacataggt gaacgtgttc aaagccaagc      2220
aaaatgcaca ccctttttct gtggcaaatc gtctctgtac atgtgtgtac atattagaaa     2280
gggaagatgt taagatatgt ggcctgtggg ttacacaggg tgcctgcagc ggtaatatat     2340
tttagaaata atatatcaaa taactcaact aactccaatt tttaatcaat tattaatttt     2400
tttttctttt taaagagaaa gcaggctttt ctagacttta aagaataaag tctttgggag     2460
gtctcacggt gtagagagga gctttgaggc caccgcaca aaattccccc agagggaaat       2520
```

-continued

```
ctcgtcggaa ggacactcac ggcagttctg gatcacctgt gtatgtcaac agaagggata    2580
ccgtctcctt gaagaggaaa ctctgtcact cctcatgcct gtctagctca tacacccatt    2640
tctctttgct tcacaggttt taaactggtt ttttgcatac tgctatataa ttctctgtct    2700
ctctctgttt atctctcccc tccctcccct cccttcttc tccatctcca ttcttttgaa     2760
tttcctcatc cctccatctc aatcccgtat ctacgcaccc ccccccccc aggcaaagca     2820 gtgctctgag tatcacatca cacaaaagga acaaaagcga acacacaaa ccagcctcaa     2880 cttacacttg gttactcaaa agaacaagag tcaatggtac ttgtcctagc gttttggaag    2940
aggaaaacag gaacccacca aaccaaccaa tcaaccaaac aaagaaaaaa ttccacaatg    3000
aaagaatgta ttttgtcttt ttgcattttg gtgtataagc catcaatatt cagcaaaatg    3060
attcctttct ttaaaaaaaa aaatgtggag gaaagtagaa atttaccaag gttgttggcc    3120
cagggcgtta aattcacaga ttttttttaac gagaaaaaca cacagaagaa gctacctcag    3180 gtgttttttac ctcagcacct tgctcttgtg tttcccttag agattttgta aagctgatag    3240
ttggagcatt ttttattttt tttaataaaa atgagttgga aaaaaaataa gatatcaact    3300
gccagcctgg agaaggtgac agtccaagtg tgcaacagct gttctgaatt gtcttccgct    3360
agccaagaac cnatatggcc ttcttttgga caaaccttga aaatgtttat tt            3412
```

<210> SEQ ID NO 7
<211> LENGTH: 1946
<212> TYPE: DNA
<213> ORGANISM: Homo sapiens
<220> FEATURE:
<221> NAME/KEY: CDS
<222> LOCATION: 1622,1702,1771,1809,1833
<223> OTHER INFORMATION: unsure of nucleotide

<400> SEQUENCE: 7

```
gctgtagcgg aggggctggg gggctgctct gtccccttcc ttgcgcgctg cggcctcagc      60
ccacccagag gccggggtgg gagggcgagt gctcagcttc ccgggttagg agccggaaaa     120
ttcaaatccg aaatattcca ccccagctcc gatgggaagt actggacagc ctgctggctc     180
agtatggtac agtagagaac tgtgagcaag tgaacaccga gagtgagacg gcagtggtga     240
atgtcaccta ttccaaccgg gagcagacca ggcaagccat catgaagctg aatggccacc     300
agttggagaa ccatgccctg aaggtctcct acatccccga tgagcagata gcacagggac     360
ctgagaatgg gcgccgaggg ggctttggct ctcgggtca gccccgccag ggctcacctg     420
tggcagcggg ggccccagcc aagcagcagc aagtggacat ccccccttcgg ctcctggtgc     480 ccacccagta tgtgggtgcc attattggca aggaggggc caccatccgc aacatcacaa     540
aacagaccca gtccaagata gacgtgcata ggaaggagaa cgcaggtgca gctgaaaaag     600
ccatcagtgt gcactccacc cctgagggct gctcctccgc ttgtaagatg atcttggaga     660
ttatgcataa agaggctaag gacaccaaaa cggctgacga ggttcccctg aagatcctgg     720
cccataataa ctttgtaggg cgtctcattg gcaaggaagg acggaacctg aagaaggtag     780
agcaagatac cgagacaaaa atcaccatct cctcgttgca agaccttacc ctttacaacc     840
ctgagaggac catcactgtg aaggggccca tcgagaattg ttgcagggcc gagcaggaaa     900
taatgaagaa agttcgggag gcctatgaga atgatgtggc tgccatgagc tctcacctga    960
tccctggcct gaacctggct gctgtaggtc ttttcccagc ttcatccagc gcagtcccgc    1020
cgcctcccag cagcgttact ggggctgctc cctatagctc ctttatgcag gctcccgagc    1080
aggagatggt gcaggtgttt atccccgccc aggcagtggg cgccatcatc ggcaagaagg    1140
```

```
ggcagcacat caaacagctc tcccggtttg ccagcgcctc catcaagatt gcaccacccg    1200
aaacacctga ctccaaagtt cgtatggtta tcatcactgg accgccagag gcccaattca    1260
aggctcaggg aagaatctat ggcaaactca aggaggagaa cttctttggt cccaaggagg    1320
aagtgaagct ggagacccac atacgtgtgc cagcatcagc agctggccgg gtcattggca    1380
aaggtggaaa aacggtgaac gagttgcaga atttgacggc agctgaggtg gtagtaccaa    1440
gagaccagac ccctgatgag aacgaccagg tcatcgtgaa aatcatcgga catttctatg    1500
ccagtcagat ggctcaacgg aagatccgag acatcctggc ccaggttaag cagcagcatc    1560
agaagggaca gagtaaccag gcccaggcac ggaggaagtg accagcccct ccctgtccct    1620
tngagtccag acaacaacg gcagaaatc gagagtgtgc tctccccggc aggcctgaga    1680
atgagtggga atccgggaca cntgggccgg gctgtagatc aggtttgccc acttgattga    1740
gaaagatgtt ccagtgagga accctgatct ntcagcccca acacccacc caattggccc    1800 aacactgtnt gccccctcggg gtgtcagaaa ttntagcgca aggcactttt aaacgtggat    1860
tgtttaaaga agctctccag gccccaccaa gagggtggat cacacctcag tgggaagaaa    1920
aataaaattt ccttcaggtt ttaaaa                                         1946
```

<210> SEQ ID NO 8
<211> LENGTH: 3283
<212> TYPE: DNA
<213> ORGANISM: Homo sapiens
<220> FEATURE:
<221> NAME/KEY: CDS
<222> LOCATION: 3243
<223> OTHER INFORMATION: unsure of nucleotide

<400> SEQUENCE: 8

```
ggcagcggag gaggcgagga gcgccgggta ccgggccggg ggagccgcgg gctctcgggg     60
aagagacgga tgatgaacaa gctttacatc gggaacctga gccccgccgt caccgccgac    120
gacctccggc agctctttgg ggacaggaag ctgcccctgg cgggacaggt cctgctgaag    180
tccggctacg ccttcgtgga ctaccccgac cagaactggg ccatccgcgc catcgagacc    240
ctctcgggta aagtggaatt gcatgggaaa atcatggaag ttgattactc agtctctaaa    300
aagctaagga gcaggaaaat tcagattcga acatccctc ctcacctgca gtgggaggtg    360
ttggatggac ttttggctca atatgggaca gtggagaatg tggaacaagt caacacagac    420
acagaaaccg ccgttgtcaa cgtcacatat gcaacaagag aagaagcaaa aatagccatg    480
gagaagctaa gcgggcatca gtttgagaac tactccttca agatttccta catcccggat    540
gaagaggtga gctccccttc gccccctcag cgagcccagc gtggggacca ctcttcccgg    600
gagcaaggcc acgcccctgg gggcacttct caggccagac agattgattt cccgctgcgg    660
atcctggtcc ccacccagtt tgttggtgcc atcatcggaa aggagggctt gaccataaag    720
aacatcacta gcagaccca gtcccgggta gatatccata gaaagagaa ctctggagct    780 gcagagaagc ctgtcaccat ccatgccacc cagagggga cttctgaagc atgccgcatg    840
attcttgaaa tcatgcagaa agaggcagat gagaccaaac tagccgaaga gattcctctg    900
aaaatcttgg cacacaatgg cttggttgga agactgattg gaaagaagg cagaaatttg    960 aagaaaattg aacatgaaac agggaccaag ataacaatct catctttgca ggatttgagc    1020
atatacaacc cggaaagaac catcactgtg aagggcacag ttgaggcctg tgccagtgct    1080
gagatagaga ttatgaagaa gctgcgtgag gcctttgaaa atgatatgct ggctgttaac    1140
acccactccg gatacttctc cagcctgtac ccccatcacc agtttggccc gttcccgcat    1200
```

```
catcactctt atccagagca ggagattgtg aatctcttca tcccaaccca ggctgtgggc      1260
gccatcatcg ggaagaaggg ggcacacatc aaacagctgg cgagattcgc cggagcctct      1320
atcaagattg cccctgcgga aggcccagac gtcagcgaaa ggatggtcat catcaccggg      1380
ccaccggaag cccagttcaa ggcccaggga cggatctttg ggaaactgaa agaggaaaac      1440
ttctttaacc ccaaagaaga agtgaagctg aagcgcata tcagagtgcc ctcttccaca       1500
gctggccggg tgattggcaa aggtggcaag accgtgaacg aactgcagaa cttaaccagt      1560
gcagaagtca tcgtgcctcg tgaccaaacg ccagatgaaa atgaggaagt gatcgtcaga      1620
attatcgggc acttctttgc tagccagact gcacagcgca agatcaggga aattgtacaa      1680
caggtgaagc agcaggagca gaaatacct cagggagtcg cctcacagcg cagcaagtga       1740
ggctcccaca gcaccagca aaacaacgga tgaatgtagc ccttccaaca cctgacagaa       1800
tgagaccaaa cgcagccagc cagatcggga gcaaaccaaa gaccatctga ggaatgagaa      1860
gtctgcggag gcggccaggg actctgccga ggccctgaga accccagggg ccgaggaggg      1920
gcggggaagg tcagccaggt ttgccagaac caccgagccc cgcctcccgc ccccagggc       1980 ttctgcaggc ttcagccatc cacttcacca tccactcgga tctctcctga actcccacga      2040
cgctatccct tttagttgaa ctaacatagg tgaacgtgtt caaagccaag caaaatgcac      2100 acccttttc tgtggcaaat cgtctctgta catgtgtgta catattagaa agggaagatg       2160
ttaagatatg tggcctgtgg gttacacagg gtgcctgcag cggtaatata ttttagaaat      2220
aatatatcaa ataactcaac taactccaat ttttaatcaa ttattaattt tttttctttt     2280
ttaaagagaa agcaggcttt tctagacttt aaagaataaa gtctttggga ggtctcacgg      2340
tgtagagagg agctttgagg ccacccgcac aaaattcacc cagagggaaa tctcgtcgga     2400
aggacactca cggcagttct ggatcacctg tgtatgtcaa cagaagggat accgtctcct      2460
tgaagaggaa actctgtcac tcctcatgcc tgtctagctc atacacccat ttctctttgc     2520
ttcacaggtt ttaaactggt tttttgcata ctgctatata attctctgtc tctctctgtt     2580
tatctctccc ctccctcccc tccccttctt ctccatctcc attcttttga atttcctcat     2640
ccctccatct caatcccgta tctacgcacc ccccccccc caggcaaagc agtgctctga     2700
gtatcacatc acacaaaagg aacaaaagcg aaacacacaa accagcctca acttacactt     2760
ggttactcaa aagaacaaga gtcaatggta cttgtcctag cgttttggaa gaggaaaaca    2820
ggaacccacc aaaccaacca atcaaccaaa caaagaaaaa attccacaat gaaagaatgt     2880
attttgtctt tttgcatttt ggtgtataag ccatcaatat tcagcaaaat gattcctttc    2940
tttaaaaaaa aaaatgtgga ggaaagtaga aatttaccaa ggttgttggc ccagggcgtt    3000
aaattcacag attttttta cgagaaaaac acacagaaga agctacctca ggtgttttta    3060
cctcagcacc ttgctcttgt gtttccctta gagattttgt aaagctgata gttggagcat    3120 tttttattt ttttaataaa aatgagttgg aaaaaaaata agatatcaac tgccagcctg     3180
gagaaggtga cagtccaagt gtgcaacagc tgttctgaat tgtcttccgc tagccaagaa    3240
ccnatatggc cttcttttgg acaaaccttg aaaatgttta ttt                       3283
```

<210> SEQ ID NO 9
<211> LENGTH: 21
<212> TYPE: DNA
<213> ORGANISM: Homo sapiens
<220> FEATURE:

```
<400> SEQUENCE: 9
gaaagtatct tcaaggacgc c                                              21

<210> SEQ ID NO 10
<211> LENGTH: 22
<212> TYPE: DNA
<213> ORGANISM: Homo sapiens
<220> FEATURE:

<400> SEQUENCE: 10
ctgcaagggg ttttgctggg cg                                             22

<210> SEQ ID NO 11
<211> LENGTH: 22
<212> TYPE: DNA
<213> ORGANISM: Homo sapiens
<220> FEATURE:

<400> SEQUENCE: 11
tccttgcgcg ctgcggcctc ag                                             22

<210> SEQ ID NO 12
<211> LENGTH: 23
<212> TYPE: DNA
<213> ORGANISM: Homo sapiens
<220> FEATURE:

<400> SEQUENCE: 12
ccaactggtg gccattcagc ttc                                            23

<210> SEQ ID NO 13
<211> LENGTH: 22
<212> TYPE: DNA
<213> ORGANISM: Homo sapiens
<220> FEATURE:

<400> SEQUENCE: 13
gctctttggg gacaggaagg tc                                             22

<210> SEQ ID NO 14
<211> LENGTH: 22
<212> TYPE: DNA
<213> ORGANISM: Homo sapiens
<220> FEATURE:

<400> SEQUENCE: 14
gacgttgaca acggcggttt ct                                             22

<210> SEQ ID NO 15
<211> LENGTH: 12
<212> TYPE: DNA
<213> ORGANISM: artificial sequence
<220> FEATURE:
<221> NAME/KEY: adaptor
<222> LOCATION: 1...12
<223> OTHER INFORMATION: synthetic adaptor sequence

<400> SEQUENCE: 15
aatttgcggt ga                                                        12

<210> SEQ ID NO 16
<211> LENGTH: 12
<212> TYPE: DNA
<213> ORGANISM: artificial sequence
```

```
<220> FEATURE:
<221> NAME/KEY: adaptor
<222> LOCATION: 1...12
<223> OTHER INFORMATION: synthetic adaptor sequence

<400> SEQUENCE: 16
aatttgttca tg                                                             12

<210> SEQ ID NO 17
<211> LENGTH: 12
<212> TYPE: DNA
<213> ORGANISM: artificial sequence
<220> FEATURE:
<221> NAME/KEY: adaptor
<222> LOCATION: 1...12
<223> OTHER INFORMATION: synthetic adaptor sequence

<400> SEQUENCE: 17
aattttccct cg                                                             12

<210> SEQ ID NO 18
<211> LENGTH: 24
<212> TYPE: DNA
<213> ORGANISM: artificial sequence
<220> FEATURE:
<221> NAME/KEY: adaptor
<222> LOCATION: 1...24
<223> OTHER INFORMATION: synthetic adaptor sequence

<400> SEQUENCE: 18
agcactctcc agcctctcac catg                                                24

<210> SEQ ID NO 19
<211> LENGTH: 23
<212> TYPE: DNA
<213> ORGANISM: artificial sequence
<220> FEATURE:
<221> NAME/KEY: adaptor
<222> LOCATION: 1...23
<223> OTHER INFORMATION: synthetic adaptor sequence

<400> SEQUENCE: 19
accgacgtcg actatcatgc atg                                                 23

<210> SEQ ID NO 20
<211> LENGTH: 24
<212> TYPE: DNA
<213> ORGANISM: artificial sequence
<220> FEATURE:
<221> NAME/KEY: adaptor
<222> LOCATION: 1...24
<223> OTHER INFORMATION: synthetic adaptor sequence

<400> SEQUENCE: 20
aggcaactgt gctatccgag catg                                                24

<210> SEQ ID NO 21
<211> LENGTH: 8
<212> TYPE: DNA
<213> ORGANISM: artificial sequence
<220> FEATURE:
<221> NAME/KEY: adaptor
<222> LOCATION: 1...8
<223> OTHER INFORMATION: synthetic adaptor sequence

<400> SEQUENCE: 21 gtgagagg                                                                   8
```

```
                                    -continued
<210> SEQ ID NO 22
<211> LENGTH: 8
<212> TYPE: DNA
<213> ORGANISM: artificial sequence
<220> FEATURE:
<221> NAME/KEY: adaptor
<222> LOCATION: 1...8
<223> OTHER INFORMATION: synthetic adaptor sequence

<400> SEQUENCE: 22 catggatg                                                                8

<210> SEQ ID NO 23
<211> LENGTH: 8
<212> TYPE: DNA
<213> ORGANISM: artificial sequence
<220> FEATURE:
<221> NAME/KEY: adaptor
<222> LOCATION: 1...8
<223> OTHER INFORMATION: synthetic adaptor sequence

<400> SEQUENCE: 23 ctcggata                                                                8
```